(12) United States Patent
Bergeon et al.

(10) Patent No.: US 8,712,933 B2
(45) Date of Patent: Apr. 29, 2014

(54) SYSTEMS AND METHODS FOR DETERMINING MUSCLE FORCE THROUGH DYNAMIC GAIN OPTIMIZATION OF A MUSCLE PID CONTROLLER FOR DESIGNING A REPLACEMENT PROSTHETIC JOINT

(71) Applicant: LifeModeler, Inc., San Clemente, CA (US)

(72) Inventors: Milton Scott Bergeon, Irvine, CA (US); David Brian Jackson, Mission Viejo, CA (US); Shawn Patrick McGuan, San Clemente, CA (US)

(73) Assignee: LifeModeler, Inc., San Clemente, CA (US)

( * ) Notice: Subject to any disclaimer, the term of this patent is extended or adjusted under 35 U.S.C. 154(b) by 0 days.

(21) Appl. No.: 13/786,623

(22) Filed: Mar. 6, 2013

(65) Prior Publication Data
US 2013/0191101 A1 Jul. 25, 2013

Related U.S. Application Data

(62) Division of application No. 12/860,326, filed on Aug. 20, 2010, now Pat. No. 8,412,669.

(60) Provisional application No. 61/236,006, filed on Aug. 21, 2009.

(51) Int. Cl.
*G06F 15/18* (2006.01)

(52) U.S. Cl.
USPC ............. 706/12; 600/595; 600/546; 623/66.1

(58) Field of Classification Search
USPC ................ 706/12, 45, 62; 600/587, 595, 546; 623/66.1
See application file for complete search history.

(56) References Cited

U.S. PATENT DOCUMENTS

| | | | |
|---|---|---|---|
| 2007/0219639 A1* | 9/2007 | Otto et al. ................. | 623/20.19 |
| 2008/0275567 A1* | 11/2008 | Makower et al. .......... | 623/23.41 |
| 2008/0294258 A1* | 11/2008 | Revie et al. ................ | 623/16.11 |
| 2010/0010506 A1* | 1/2010 | Murphy ....................... | 606/130 |

* cited by examiner

*Primary Examiner* — David Vincent
(74) *Attorney, Agent, or Firm* — David Chambers

(57) ABSTRACT

Systems and methods for determining muscle force are presented. Proportional, integral, and derivative control is used to simulate muscle forces for multiple muscles contributing to a kinematic profile. The simulated muscle forces are modified by dynamic gains that are calculated in order to achieve a muscle recruitment objective such as minimizing collective muscle effort while still achieving the kinematic motion.

5 Claims, 4 Drawing Sheets

SYSTEMS AND METHODS FOR DETERMINING MUSCLE FORCE THROUGH DYNAMIC GAIN OPTIMIZATION OF A MUSCLE PID CONTROLLER FOR DESIGNING A REPLACEMENT PROSTHETIC JOINT

RELATED APPLICATION

The present application is a divisional of U.S. application Ser. No. 12/860,326 filed Aug. 20, 2010, and claims the benefit of U.S. provisional patent application No. 61/236,006, filed Aug. 21, 2009, which is incorporated herein by reference in its entirety.

BACKGROUND

1. Field of the Invention

The invention relates generally to control schemes. In one embodiment, a system for optimizing a proportional, integral, derivative (PID) controller through the use of dynamic gains is disclosed.

2. Related Art

One of the major objectives of a biomechanical simulation tool is to determine the physiologically relevant muscle forces required for a given muscular-skeletal model performing a prescribed kinematic profile. Examples of kinematic profiles include the flexion of elbow or knee. However, kinematic profiles may also be more complex. For example, a kinematic profile may include the motion of walking. For many models and kinematic profiles there are multiple muscle activations that are possible. The goal of the simulation then becomes choosing the set of muscle activations, or muscle recruitment patterns, that best match what is expected for human motion. A typical assumption for this goal is the recruitment pattern that produces the minimum amount of muscle force while maintaining the kinematic profile and physiological limits. Other assumptions, or goals, are possible. For optimization, the problem being solved is a determination of the solution that best meets the desired muscle recruitment goal.

One solution approach used involves performing a static optimization. This approach directly optimizes muscle forces, within physiological limits, at sequential time steps via a quasi-dynamic, or static solution. Dynamic forward analysis, using the prescribed muscle force values, is then performed over some small time period during which the muscle forces are held constant prior to starting the next static solution.

There are two major limitations to this approach. First, it is based on sequential static solutions rather than a true dynamic solution. This has potential accuracy problems due to the limitation that the muscle forces are fixed over the time period between static solutions, rather than being a truly dynamically varying muscle force as would be the case with real muscles.

The second limitation is related to solution formulation. Since the static optimization formulation is a direct force optimization, there is not an opportunity to take advantage of a proportional-integral-derivative (PID) based force controller. The advantages of the PID control approach, namely solution stability and speed, are therefore given up in order to directly determine muscle forces through optimization.

Another solution approach involves using a PID control system for determining muscle force, with a separate PID controller for each muscle represented in the system. A classical PID control system uses proportional, integral, and derivative terms of an error function to generate a control signal which is fed back into the system. Typically each control term is multiplied by a constant gain that is set prior to running the system. Some biomechanical simulations of muscular-skeletal systems have used a PID control scheme, e.g. LifeMOD, for determining muscle forces required to meet a pre-determined kinematic profile. This is done by using a sensor of the muscle kinematics, e.g. muscle length, muscle velocity, or joint angle, which is compared to a target signal. Output of the control system is a muscle control force that may further be modified to physiological limitations based on maximum force, velocity, etc.

The PID control scheme is an efficient and stable approach for determining muscle forces in a model required to meet the prescribed kinematic profile. For situations where multiple muscle activations, or recruitment patterns, are able to meet the same kinematic profile, however, the approach does not preferentially choose the solution that has the minimum force, or any other assumed recruitment objective. Thus, an improved system for determining muscle forces in a model is desirable.

SUMMARY

In one aspect, a computer implemented system for simulating muscle forces is provided. The system includes an interface module configured to obtain a muscle recruitment objective, an analysis module configured to determine one or more dynamic gains based on the muscle recruitment objective, and a feedback control loop module configured to determine muscle forces based, at least in part; on the one or more dynamic gains and on proportional, integral, and derivative (PID) control.

In another aspect, a computer readable medium storing instructions that, when executed by a computer, cause the computer to perform a method for simulating muscle forces is provided. The method includes determining a kinematic profile, determining a first muscle that contributes to the kinematic profile, determining a second muscle that contributes to the kinematic profile, and determining muscle forces for the first and second muscles that meet the kinematic profile and minimize collective muscle effort.

In another aspect, a method for designing a replacement join is presented. The method includes determining a kinematic profile associated with joint, determining a first muscle that contributes to the kinematic profile, determining a second muscle that contributes to the kinematic profile, determining muscle forces for the first and second muscles that meet the kinematic profile and minimize collective muscle effort; and modifying the replacement joint based, at least in part, on the muscle forces.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DESCRIPTION OF THE INVENTION

Embodiments of the current invention take advantage of the PID muscle force control (e.g., speed and accuracy of the solution kinematics and muscle physiological limits) and add a desired recruitment goal as defined by an optimization objective. A benefit associated with present embodiments is that the resultant solution remains a true dynamic solution using PID controllers, so the solution remains fast and accurate.

Embodiments of the current invention extend a PID-based muscle force algorithm to include a direct dynamic optimization of PID time-varying gains such that the resulting PID-based muscle force will directly generate muscle forces optimized to meet a user defined objective, while maintaining physiological force limits and kinematic profiles. The objective of the optimization may be to minimize the collective effort each of the muscles. The collective effort of the muscles may be represented by the sum squared muscle forces, the sum squared activation levels, maximum activation, or any other meaningful criteria. Other optimization objectives could also be used.

In some embodiments, the muscle formulation may be modified so that it contains a time varying muscle gain function, e.g. a spline of values. Optimization may be based on a series of local time optimizations, performed over a small time period, such that the PID controller continues to function but the gains are adjusted to meet the optimization objective within the time period of interest. A series of optimizations, strung together sequentially, may then define a time varying gain profile for the muscles. The gain profile may represent the relative strength of the individual muscle controllers at each instance of time required to meet the optimization objective. The output of the muscles may be optimized muscle forces that continue to meet the physiological limits of the muscle, as defined by the original unmodified PID-based muscle force engine, while simultaneously meeting the optimization objective.

Figure 1:
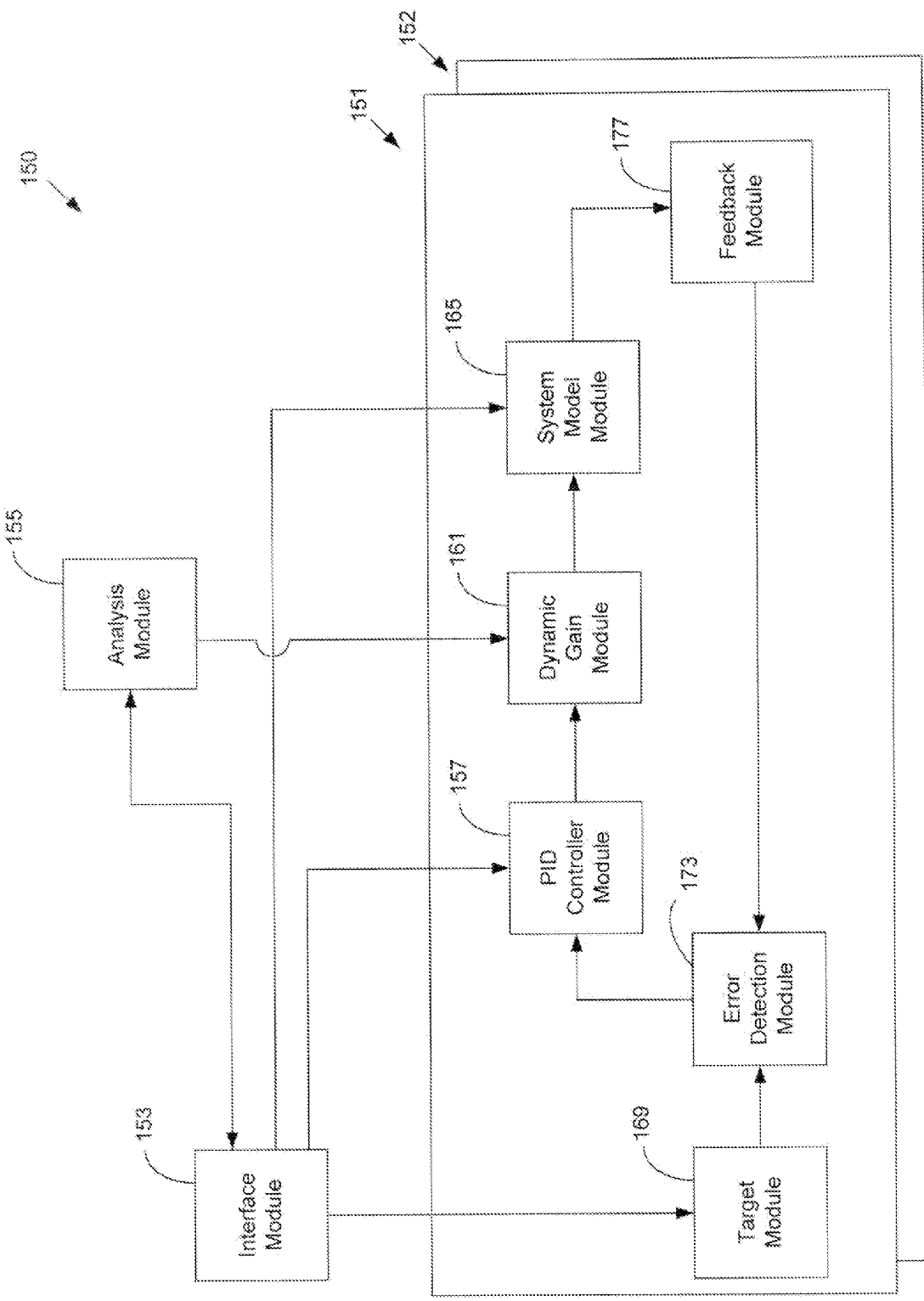
FIG. 1 is a functional block diagram illustrating an example system for muscle simulation that may be used in conjunction with various embodiments described herein.

FIG. 1 is a functional block diagram illustrating an example system 150 for muscle simulation. In one embodiment, the system 150 is a computer implemented system for simulating muscle forces. The system 150 may be implemented as a processor executing instructions for carrying out the functionality described herein. The system 150 may also comprise one or more input devices such as a mouse or keyboard (not shown). The system 150 may also comprise one or more output devices such as a monitor (not shown). The system 150 comprises an interface module 153, an analysis module 155, a PID controller Module 157, a dynamic gain module 161, a system model module 165, a feedback module 177, an error detection module 173 and a target module 169. The PID controller Module 157, dynamic gain module 161, system model module 165, feedback module 177, error detection module 173, and target module 169 may be collectively referred to as a feedback control loop module 151.

Simulations of kinematic profiles may involve multiple muscles. Each individual muscle in a simulation may have a separate control loop 151. System 150 comprises first and second control loops 151 and 152. Fewer or more control loops may be implemented depending on the number of muscles involved in a simulation. The particular muscles involved in a simulation may be determined by models for particular kinematic profiles. For example, a model reflecting the biomechanics of a body may identify a set of muscles that contribute to a particular kinematic profile. Alternatively, the muscles involved in a particular simulation may be selected by a user based on criteria such as a threshold contribution to a kinematic profile. The set of control loops for muscles in a simulation may share a single interface module 153 and analysis module 155.

The interface module 153 is configured to interact with a user and to receive information from the use relating to the simulation. For example, the interface module 153 may comprise a display, a keyboard, mouse, microphone, or other device capable of receiving information from or communicating information to a user. This information received by the interface module 153 may include details on kinematic profiles to be performed, static gains for the PID controller module, muscle recruitment objectives, system model information, or other information.

The interface module 153 may also communicate information relating to the simulation, e.g., results, dynamic gain values, or other information to the user. The interface module provides obtained information to the other modules in the system 150. For example, in one embodiment, input on the kinematic profile to be performed is communicated to the target module 169. The target module can then supply a target kinematic measurement, such as muscle length, muscle velocity, joint angle, or other kinematic measure, to the error detection module 173 in order to facilitate accurate simulation of the desired kinematic profile. The error detection module 173 determines the difference between a target kinematic measurement provided by the target module 169 and the current simulated value of the kinematic module as provided by the feedback module 177. The difference between the target and simulated value is communicated to the PID controller module 157 which determines updated muscle forces based on the error. In particular, the PID controller module 157 determines updated muscle forces that take into account one or more of the error (proportional), the accumulated error over a period of time (integral), and the change in error over a period of time (derivative). Each type of error compensation affecting the updated muscle force may have a separate static gain that affects its weight relative to the other types of error compensation. These static gain coefficients may be communicated to the PID controlled module 157 by the interface module 153.

The updated muscle force from the PID controller module 157 is communicated to a dynamic gain module 161. The dynamic gain module 161 applies a dynamic gain to the updated muscle force determined by the PID controller 157. The effect of the dynamic gain module 161 is represented by equation 1 below:

$$F = A(t) * (P_{gain} * P_{error} + I_{gain} * I_{error} + D_{gain} * D_{error}) \qquad \text{Eq. (1)}$$

In equation 1, F represents the optimized muscle force. $A(t)$ represents the dynamic gain. $P_{gain}$ represents the static gain for proportional error. $P_{error}$ represents the proportional error. $I_{gain}$ represents the static gain for integral error. $I_{error}$ represents the integral error. $D_{gain}$ represents the static gain for derivative error. $D_{error}$ represents derivative error.

After multiplying the collective PID term by the dynamic gain $A(t)$, the resulting optimized force is communicated to the system model module 165. The system model module 165 modifies the optimized according to general biomechanical system constraints including, for example, physiological limitations on muscle force. The output of the system model module 165 is then communicated to the feedback module 177. In one embodiment, the feedback module 177 acts a sensor for taking a kinematic measurement, e.g., muscle length, from the output of the system model module 165 for comparison against the target value by the error detection module 173. In this manner, the output of the system model module is fed back so that the subsequent error can be determined and the system 150 can adjust in order to match the desired kinematic profile.

As described above, traditional PID controllers do not take into account factors other than kinematic accuracy. Thus, where multiple muscle recruitment patterns can result in the same kinematic measurement, traditional PID controllers do not provide a way to distinguish or select a better recruitment pattern. Advantageously, the dynamic gain module 161 permits the system 150 to differentiate between recruitment profiles. In particular, a user can specify a muscle recruitment objective, e.g., minimization of muscle activation, which is then implemented through the dynamic gain module 161. Thus, the benefits of using a PID controller can be achieved while also allowing the user to determine a muscle recruitment pattern that meets criteria other than kinematic accuracy.

In one embodiment, muscle recruitment objectives are met by controlling the dynamic gain values. As described above, each muscle involved in a simulation can have a separate control loop, e.g., control loops 151 and 152, and a separate dynamic gain, A(t). In one embodiment, muscle recruitment objectives can be met by optimizing the dynamic gains for some or all of the muscles in a simulation. For example, a user muscle recruitment goal may be to minimize a measurement related to muscle forces across all muscles. This goal may be represented by equation 2.

$$G = \mathrm{Sum}_{i=1,N}(F_i)^a \qquad \text{Eq. (2)}$$

In equation 2, G represents the value to be minimized, i is an index of the current muscle, N is the number of muscles in the simulation, $F_i$, is the force for the current muscle, and a is a value specified by the user, e.g., 2 or greater. In the system 150, the analysis module 155 is configured to receive a muscle recruitment objective from the interface module 153 and to determine dynamic gains for one or more muscles based on the muscle recruitment objective. For example, in one embodiment, the analysis module 155 minimizes G at time intervals selected by the user.

One benefit associated with the present embodiments is that the size of the time steps used for definition of the optimization cycle in determining dynamic gains is decoupled from the accuracy of the underlying kinematic accuracy. Consequently, this allows for fairly large time steps for the optimization loop, which results in much faster computational solutions without compromising the kinematic accuracy of the solution.

It will be appreciated that while the embodiment of FIG. 1 has been described in relationship to muscle simulation, the systems and methods described herein may be implemented in other applications as well. In particular, using dynamic gains in a PID system to achieve compliance with a user selected criteria may be implemented in other applications.

Figure 2:
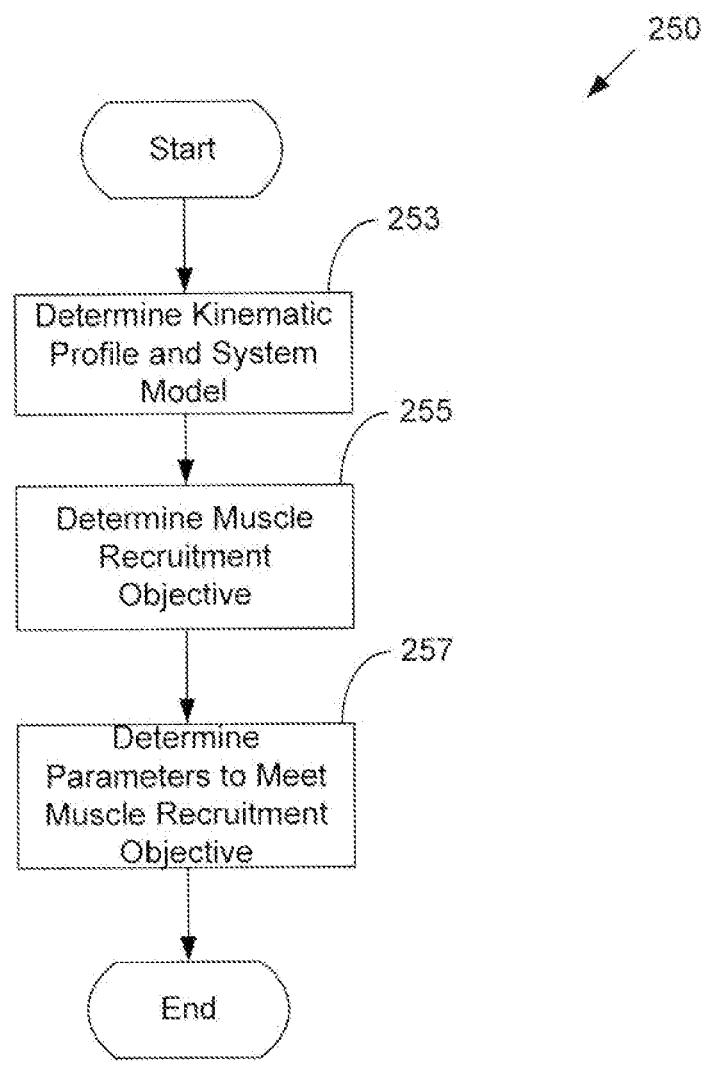
FIG. 2 is a flow chart illustrating an example method for muscle simulation that may be used in conjunction with various embodiments described herein.

FIG. 2 is a flow chart illustrating an example method for muscle simulation that may be used in conjunction with various embodiments described herein. The method 250 may be performed by the system 150 of FIG. 1. At step 253, the system determines a kinematic profile to be simulated and a system model. As described above, the profile and the system model may be supplied by a user. For example, the profile and system model may be entered using software such as Life-MOD, available from LifeModeler, Inc. that is running on a computer implementing the system. Alternatively, the profile and system model may be retrieved from memory in a computer implementing the system. In one embodiment, the kinematic profile represents the flexion of the right forearm from the elbow. In this embodiment, the system model defines the general biomechanical system properties and constraints of the plurality of muscles used in the kinematic profile. Step 253 may also involve determining one or more muscles that contribute to the determined kinematic profile. For example, based on the kinematic profile and the system model, the system may determine that first and second muscles can contribute to the performance of the kinematic profile.

Continuing at step 255, the system determines a muscle recruitment objective. Examples of muscle recruitment objectives include, but are not limited to, minimizing muscle activation. The muscle recruitment objective may be supplied by a user. For example, the objective may be entered using the LifeMOD software described above. Alternatively, the objective may obtained from memory in a computer implementing the system. In one embodiment, the muscle recruitment objective is to minimize muscle activation or muscle force for all muscles performing the kinematic profile. At step 257, the system determines parameters to meet the muscle recruitment objective. For example, as described above, this may include determining dynamic gains for the PID controllers of the muscles in the system based on the muscle recruitment objective. In one example, this may involve minimizing the muscle activation or muscle force for all muscles in the simulation. This optimization process may be performed periodically during the simulation at intervals separate from the size of the time steps in the simulation. Optionally, the dynamic gains, the unoptimized activation levels, the optimized recruitment levels, or other information may also be output to a user.

Figure 3:
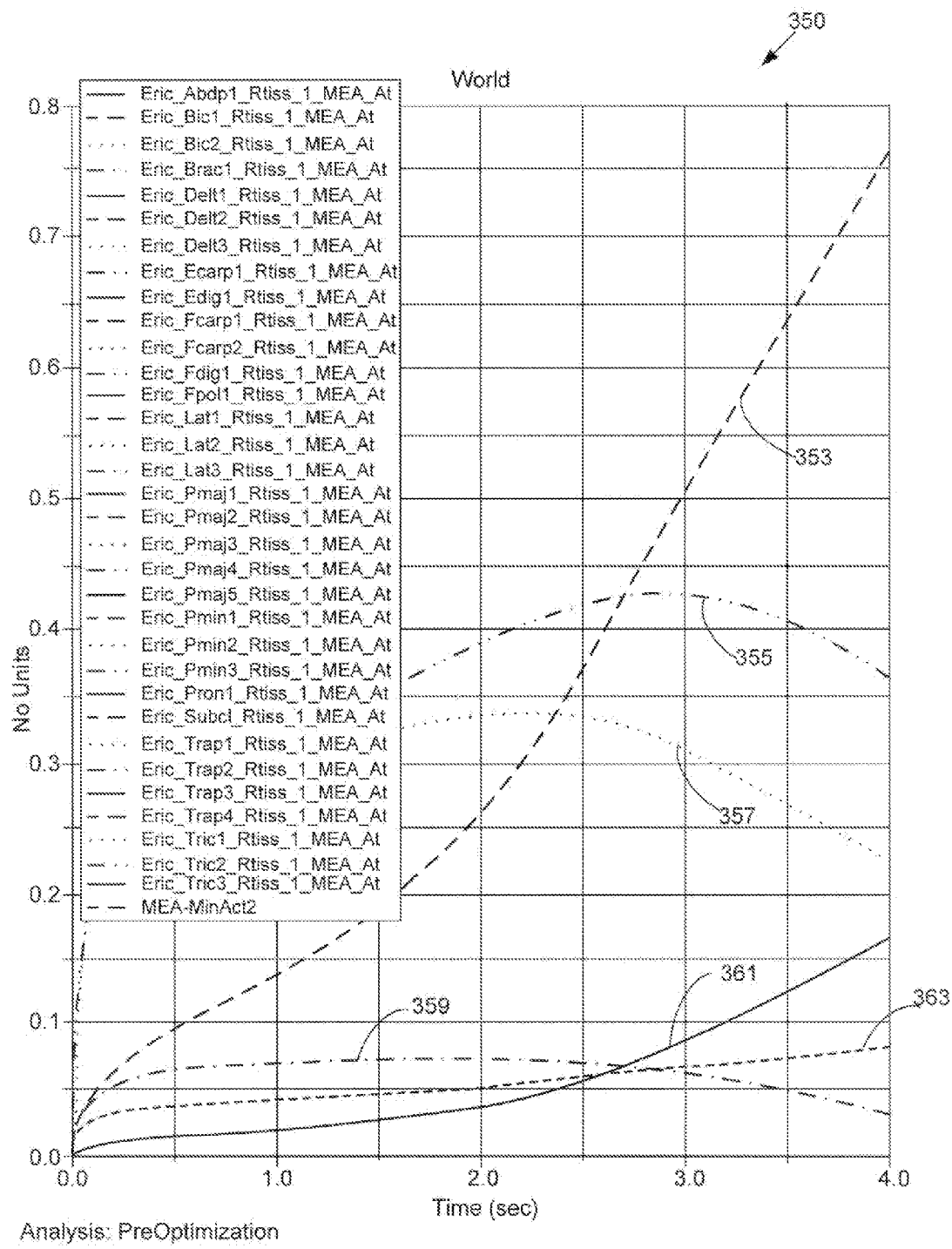
FIG. 3 is an illustration of pre-optimization activation levels for muscles involved a particular kinematic profile.

FIG. 3 is an illustration of pre-optimization activation levels for muscles involved in the kinematic profile described above with respect to FIG. 2. In particular, the activation levels 353, 355, 357, 359, 361, and 363, correspond to unoptimized activation levels for six muscles which are predominately involved in the flexion of the right forearm at the elbow.

Figure 4:
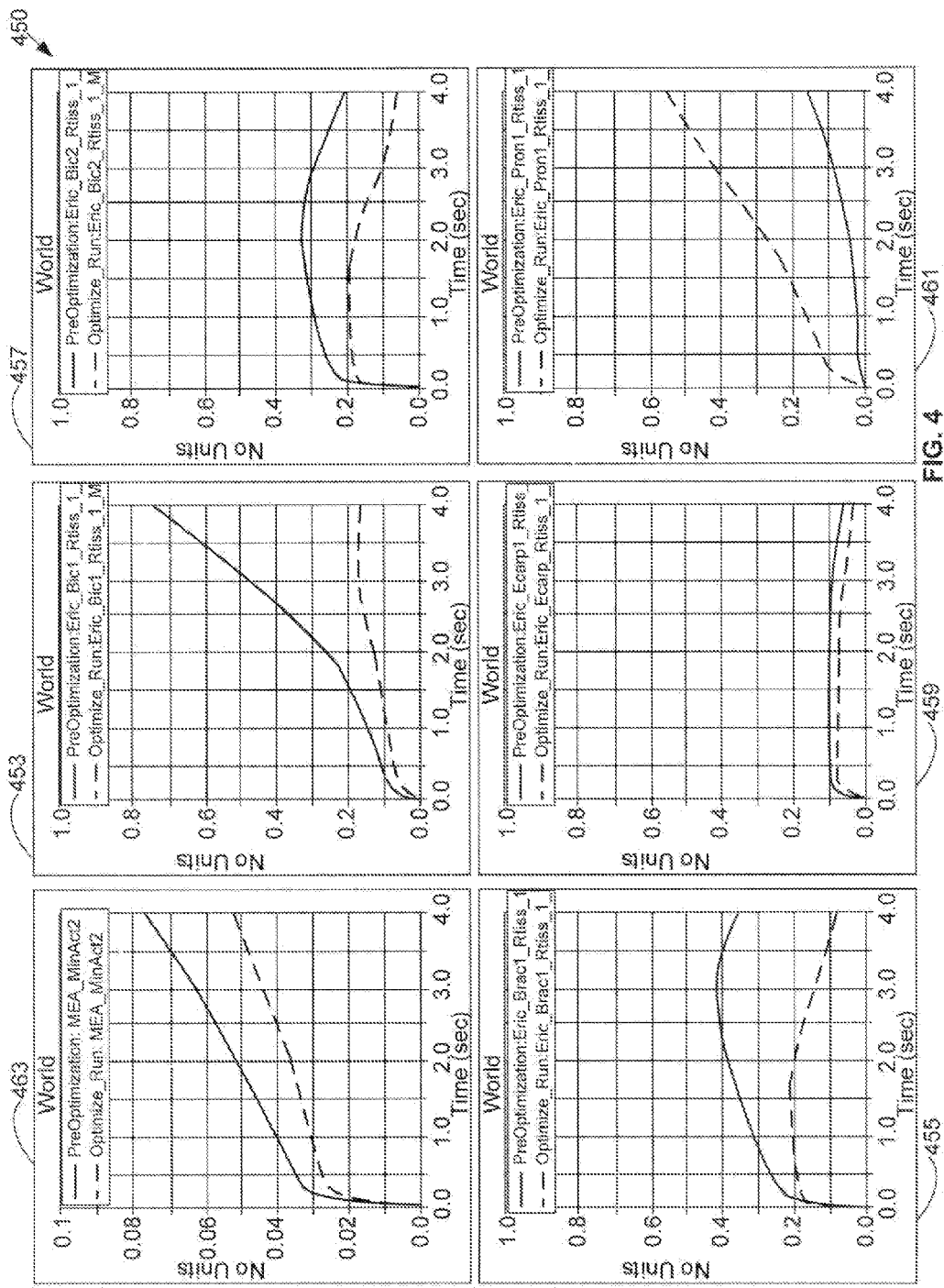
FIG. 4 is an illustration of pre and post optimization activation levels for muscles involved in a particular kinematic profile.

FIG. 4 is an illustration of pre- and post-optimization activation levels for muscles involved in the kinematic profile described above with respect to FIGS. 2 and 3. The chart 453 corresponds to the activation level 353 of FIG. 3. Similarly, the charts 455, 457, 459, 461, and 463 correspond respectively to the activation levels 355, 357, 359, 361, and 363 of FIG. 3. As shown the optimized activation levels are significantly lower in each of the charts with the exception of chart 461. However, overall, the total activation level of the muscles depicted has decreased. Advantageously, the use of dynamic gains in the control loop of the system allows for this optimization while still taking advantage of the benefits of PID control.

In one embodiment, the system 150 may be used to design biomechanical systems such as total knee replacements, other replace joints, spinal implants, or other devices. For example, a total knee replacement design system can include a system for simulating muscle forces involved in kinematic motions associated with the knee replacement. By simulating these muscle forces, the properties of knee replacement, such as its geometry, composition, stillness, or other characteristics can be modified in order to better suit its actual use in a patient's body. The concept of designing a biomechanical system that accurately replicates the function of a system in the body can be referred to a biofidelity. The systems and methods herein provide for more accurately determining muscle forces. These more accurate forces can in turn lead to more biofidelic biomechanical systems. More generally, by accurately modeling and simulating the behavior of kinematic systems, the present systems and methods facilitate the development of systems and devices with greater precision and accuracy.

Various illustrative implementations of the present invention have been described. However, one of ordinary skill in the art will see that additional implementations are also possible and within the scope of the present invention. As was noted above, the same principles can be applied to modeling other tissue types, such as tendons and ligaments.

Accordingly, the present invention is not limited to only those implementations described above. Those of skill in the art will appreciate that the various illustrative modules and method steps described in connection with the above described figures and the implementations disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for case of description. Specific functions can be moved from one module or step to another without departing from the invention.

The various illustrative modules and method steps described in connection with the implementations disclosed herein can be implemented or performed with a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A general-purpose processor can be a microprocessor, but in the alternative, the processor can be any processor, controller, or microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the implementations disclosed herein can be embodied directly in hardware, in a software module executed by a processor, or in a combination of the two. A software module can reside in computer or machine readable storage media such as RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

The above description of the disclosed implementations is provided to enable any person skilled in the art to make or use the invention. Various modifications to these implementations will be readily apparent to those skilled in the art, and the generic principles described herein can be applied to other implementations without departing from the spirit or scope of the invention. Thus, it is to be understood that the description and drawings presented herein represent example implementations of the invention and are therefore representative of the subject matter which is broadly contemplated by the present invention. It is further understood that the scope of the present invention fully encompasses other implementations.

What is claimed is:

1. A method for designing a replacement joint prosthesis comprising:
    determining a kinematic profile associated with a joint;
    determining a first muscle that contributes to the kinematic profile;
    determining a second muscle that contributes to the kinematic profile;
    determining muscle forces for the first and second muscles that meet the kinematic profile and a muscle recruitment objective; and
    modifying the replacement joint prosthesis based, at least in part, on the muscle forces; wherein determining the muscle forces comprises determining dynamic gains from the first and second muscles using proportional, integral derivative control.

2. The method of claim 1, wherein the replacement joint prosthesis comprises a total knee replacement.

3. The method of claim 1, wherein collective muscle effort is determined in terms of the sum of the squares of the muscle forces.

4. The method of claim 1, wherein modifying the replacement joint prosthesis comprises changing the geometry, composition, or stiffness of the replacement joint prosthesis.

5. The method of claim 1, wherein the muscle recruitment objective is to minimize collective muscle effort.

* * * * *